US006429003B1

(12) United States Patent
Bedzyk et al.

(10) Patent No.: US 6,429,003 B1
(45) Date of Patent: Aug. 6, 2002

(54) GENES ENCODING DENITRIFICATION ENZYMES

(75) Inventors: Laura Anne Bedzyk, Odessa; Rick Weizhang Ye, Hockessin, both of DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/504,357

(22) Filed: Feb. 15, 2000

Related U.S. Application Data

(62) Division of application No. 09/354,129, filed on Jul. 15, 1999, now Pat. No. 6,136,588.
(60) Provisional application No. 60/093,191, filed on Jul. 17, 1998, now abandoned.

(51) Int. Cl.[7] ............................. C12N 1/21; C12N 9/14; C07H 21/04
(52) U.S. Cl. ............... 435/252.3; 435/191; 435/254.11; 435/320.1; 435/252.31; 435/254.2; 435/254.33; 536/23.1; 536/23.2; 536/23.7
(58) Field of Search .............................. 435/191, 252.3, 435/252.33, 252.31, 320.1, 254.11, 254.2; 536/23.1, 23.7, 23.2

(56) References Cited

PUBLICATIONS

Berks et al. The napEDABC cluster encoding the periplasmic nitrate reductase system of Thiosphaera pantropha, 1995, Biochem. J. 309:983–992.*
Siddiqui et al. Structure and Function of a Periplasmic Nitrate Reductase in *Alcaligenes eutrophus* H16, 1993, J. Bacteriology 175(18): 5867–5876.*
Ye et al., Appl. Environ. Microbiol 60:1053–1058 (1994).
Zumft et al., Microbiol., Mol. Biol. Rev. 61: 533–616 (1997).
Bartnikas et al., J. Bacteriol. 179:3534–3540 (1997).
de Boer et al., Eur. J. Biochem. 242: 592–600 (1996).
Reyes et al., Biochem J., 1998 331(1997).
Grove et al., Mol. Microbiol. 19, 467–481 (1996).
Zumft et al., Eur. J. Biochem 219: 481–490 (1994).
Bell et al., FEBS lett. 265:85–87 (1990).
Kastrau et al., Eur. J. Biochem. 222:293–303 (1994).
Tyson et al., Arch. Microbiol. 168: 403–411 (1997).
Bell et al., (1993), J. of General Microbiology, vol. 139, p 3205–3214.
Reyes, F et al., Mol. Microbiol. 19: 1307–1318 (1996).
Sakurai, N. et al., Biochem. Biophys. Res. Commun. 243 (2), 400–406 (1998).

* cited by examiner

Primary Examiner—Rebecca E. Prouty
Assistant Examiner—Richard Hutson

(57) ABSTRACT

This invention relates to the isolation of nucleic acid fragments from Pseudomonas sp. strain G-179 that encode periplasmic nitrate reductase and nitric oxide reductase enzymes. The enzymes are useful in denitrification reactions and for the identification of other denitrifying bacteria. In addition, this invention also relates to the construction of chimeric genes encoding all or a substantial portion of a bacterial nitric oxide reductase or a bacterial periplasmic nitrate reductase enzymes, in sense or antisense orientation, wherein the expression of the chimeric genes results in production of altered levels of the nitric oxide reductase or periplasmic nitrate reductase in a transformed host cell.

7 Claims, 1 Drawing Sheet

SEQUENCE LISTING

<160> NUMBER OF SEQ ID NOS: 14

<210> SEQ ID NO 1
<211> LENGTH: 1419
<212> TYPE: DNA
<213> ORGANISM: Pseudomonas sp. strain G-179

<400> SEQUENCE: 1

```
atgaaatacc aaactcaaaa ggtcgcgatg ctgtatttct acggcgcgat cggcctcttc      60
ctggcacagg ttttgttcgg cgttctggct ggcacgatct atgtcatgcc aaacactctt     120
tccgaactcc tgccgttcaa catcgtcaga atgatccata ccaatgcgct gatcgtttgg     180
cttttgatcg gcttcatggg ggcgacctat tacctgcttc ccgaagaggc ggaaaccgaa     240
ctctacagcc cgaaactggc gatcgcgcag ttctggatct tcctgattgc cgccgccatt     300
gcggtggtgg gctacatgtt caagatccat gagggggcgtg aatttctcga acagcccttc     360
atcatcaaga tcggcatcgt catcgtctgc ctgatgttcc tcttcaatgt caccatgaca     420
tcgctgaagg gccgcaagac cgtcgtcacc aatatcctga tcttcggtct ctgggggatt     480
gcgatcttct tcctgttctc cttctacaat ccggccaacc tcgcgctcga caagatgtac     540
```

```
tggtggtacg tcgttcatct gtgggtcgaa ggtgtgtggg agctgatcat ggcctcggtt      600
ctggccttcc tgatgatcaa gctcaacggc atcgaccgcg aagtggtcga agtggctt       660
tacgtcatcg tcggtctggc acttttctcc ggcatcctcg gcaccggtca ccactattac     720
tggatcggtg ctccgggtta ctggcagtgg atcggttcgc tgttctcgac gctcgaagtc     780
gcaccgttct tcaccatggt gatcttcacc ttcgtgatga cctggaaggc cggtcgaaaa     840
catccgaacc gcgccgctct tctgtggtcg atcggctgct cggtcatggc cttcttcggc     900
gccggcgtct ggggtttcct gcacacgctg tcctcggtga actattatac ccatggcacg     960
caggtcaccg cagcacatgg tcacctcgct ttcttcggcg cttatgtcat gctgaaccta    1020
gccatcatgg cctatgccgt tccggaaatc tgtggccgca agccgtataa ccagtggctg    1080
tccatggtgt ccttctggat gatgtgcacg gccatgtcgg tgatgacctt cgcactcact    1140
ttcgccggtg tgttgcaggt gcatctgcag cgcgtgctcg gcgagggtta catggacgtg    1200
caggaccagc tcgccctgtt ctactgggtc cgcctcggct ccggcgtctt cgtcctcatt    1260
tcggcattga tgtttgtctg ggccattctg gtgcccggca aggatcgcgt cccggctgcc    1320
agcggcatcg ctgaacggcc gagtgagcga ttccggcccg cgatcctga agccgcgggc    1380
cgggacttat cccttcatcc tcaaggaaac ctccgatga                           1419
```

<210> SEQ ID NO 2
<211> LENGTH: 472
<212> TYPE: PRT
<213> ORGANISM: Pseudomonas sp. strain G-179

<400> SEQUENCE: 2

```
Met Lys Tyr Gln Thr Gln Lys Val Ala Met Leu Tyr Phe Tyr Gly Ala
 1               5                  10                  15

Ile Gly Leu Phe Leu Ala Gln Val Leu Phe Gly Val Leu Ala Gly Thr
                20                  25                  30

Ile Tyr Val Met Pro Asn Thr Leu Ser Glu Leu Leu Pro Phe Asn Ile
            35                  40                  45

Val Arg Met Ile His Thr Asn Ala Leu Ile Val Trp Leu Leu Ile Gly
        50                  55                  60

Phe Met Gly Ala Thr Tyr Tyr Leu Leu Pro Glu Glu Ala Glu Thr Glu
 65                  70                  75                  80

Leu Tyr Ser Pro Lys Leu Ala Ile Ala Gln Phe Trp Ile Phe Leu Ile
                85                  90                  95

Ala Ala Ala Ile Ala Val Val Gly Tyr Met Phe Lys Ile His Glu Gly
               100                 105                 110

Arg Glu Phe Leu Glu Gln Pro Phe Ile Ile Lys Ile Gly Ile Val Ile
           115                 120                 125

Val Cys Leu Met Phe Leu Phe Asn Val Thr Met Thr Ser Leu Lys Gly
       130                 135                 140

Arg Lys Thr Val Val Thr Asn Ile Leu Ile Phe Gly Leu Trp Gly Ile
145                 150                 155                 160

Ala Ile Phe Phe Leu Phe Ser Phe Tyr Asn Pro Ala Asn Leu Ala Leu
               165                 170                 175

Asp Lys Met Tyr Trp Trp Tyr Val Val His Leu Trp Val Glu Gly Val
           180                 185                 190

Trp Glu Leu Ile Met Ala Ser Val Leu Ala Phe Leu Met Ile Lys Leu
       195                 200                 205

Asn Gly Ile Asp Arg Glu Val Val Glu Lys Trp Leu Tyr Val Ile Val
   210                 215                 220
```

-continued

Gly Leu Ala Leu Phe Ser Gly Ile Leu Gly Thr Gly His His Tyr Tyr
225                 230                 235                 240

Trp Ile Gly Ala Pro Gly Tyr Trp Gln Trp Ile Gly Ser Leu Phe Ser
            245                 250                 255

Thr Leu Glu Val Ala Pro Phe Phe Thr Met Val Ile Phe Thr Phe Val
        260                 265                 270

Met Thr Trp Lys Ala Gly Arg Lys His Pro Asn Arg Ala Ala Leu Leu
    275                 280                 285

Trp Ser Ile Gly Cys Ser Val Met Ala Phe Phe Gly Ala Gly Val Trp
        290                 295                 300

Gly Phe Leu His Thr Leu Ser Ser Val Asn Tyr Tyr Thr His Gly Thr
305                 310                 315                 320

Gln Val Thr Ala Ala His Gly His Leu Ala Phe Phe Gly Ala Tyr Val
                325                 330                 335

Met Leu Asn Leu Ala Ile Met Ala Tyr Ala Val Pro Glu Ile Cys Gly
            340                 345                 350

Arg Lys Pro Tyr Asn Gln Trp Leu Ser Met Val Ser Phe Trp Met Met
        355                 360                 365

Cys Thr Ala Met Ser Val Met Thr Phe Ala Leu Thr Phe Ala Gly Val
    370                 375                 380

Leu Gln Val His Leu Gln Arg Val Leu Gly Glu Gly Tyr Met Asp Val
385                 390                 395                 400

Gln Asp Gln Leu Ala Leu Phe Tyr Trp Val Arg Leu Gly Ser Gly Val
                405                 410                 415

Phe Val Leu Ile Ser Ala Leu Met Phe Val Trp Ala Ile Leu Val Pro
            420                 425                 430

Gly Lys Asp Arg Val Pro Ala Ala Ser Gly Ile Ala Glu Arg Pro Ser
        435                 440                 445

Glu Arg Phe Pro Ala Arg Asp Pro Glu Ala Ala Gly Arg Asp Leu Ser
    450                 455                 460

Leu His Pro Gln Gly Asn Leu Arg
465                 470

<210> SEQ ID NO 3
<211> LENGTH: 453
<212> TYPE: DNA
<213> ORGANISM: Pseudomonas sp. strain G-179

<400> SEQUENCE: 3
atggcagaac gcctcaccaa gaccggagcc cgcaacgtgt tttacggcgg atccatcttc    60
ttcttcgcaa ttttcgtggg gctgactgcg catagccatc ggtacatccg caccacctcc   120
acggacgaga ccaccctcaa cgacagcgtc gcccgcggca acatgtctg ggagaagaac    180 tcctgtatca attgtcatac cttgctgggc gagggcgcct atttcgcgcc tgaactcggc   240
aatgtctggg ttcgttatgg tggcaaggac gacccggaaa gcgcccgcga cagcctgaag   300
gcctggatgg cggcgcagcc ctcgggcatc gagggcggc gccagatgcc gcagttcaac   360
ctgacagaac aggaactgaa cgacctcgcc gacttcctcg aatggacgag caagatcaac   420
acccagaatt ggccgccgaa cgacgccggt tga                                453

<210> SEQ ID NO 4
<211> LENGTH: 150
<212> TYPE: PRT
<213> ORGANISM: Pseudomonas sp. strain G-179

-continued

```
<400> SEQUENCE: 4

Met Ala Glu Arg Leu Thr Lys Thr Gly Ala Arg Asn Val Phe Tyr Gly
 1               5                  10                  15

Gly Ser Ile Phe Phe Ala Ile Phe Val Gly Leu Thr Ala His Ser
            20                  25                  30

His Arg Tyr Ile Arg Thr Thr Ser Thr Asp Glu Thr Thr Leu Asn Asp
            35                  40                  45

Ser Val Ala Arg Gly Lys His Val Trp Glu Lys Asn Ser Cys Ile Asn
         50                  55                  60

Cys His Thr Leu Leu Gly Glu Gly Ala Tyr Phe Ala Pro Glu Leu Gly
 65                  70                  75                  80

Asn Val Trp Val Arg Tyr Gly Gly Lys Asp Asp Pro Glu Ser Ala Arg
                 85                  90                  95

Asp Ser Leu Lys Ala Trp Met Ala Ala Gln Pro Ser Gly Ile Glu Gly
            100                 105                 110

Arg Arg Gln Met Pro Gln Phe Asn Leu Thr Glu Gln Glu Leu Asn Asp
            115                 120                 125

Leu Ala Asp Phe Leu Glu Trp Thr Ser Lys Ile Asn Thr Gln Asn Trp
        130                 135                 140

Pro Pro Asn Asp Ala Gly
145             150

<210> SEQ ID NO 5
<211> LENGTH: 798
<212> TYPE: DNA
<213> ORGANISM: Pseudomonas sp. strain G-179

<400> SEQUENCE: 5
atgcatctgc gtcacgcgac ctcccagatc ccggcctatg cgccggccgg caatgaatgc     60
gccctgttcg aaaccgcctg gacacgccag ttgccgctgc tgctgaaagg cccgaccggc    120
tgcggcaaga cccgtttcgt cggccatatg gcggcaaagc ttggcctgcc gctggccacc    180
gtctcctgcc atgacgatct ggccgccgcc gacctgaccg ccgttacct cctgaagggc     240 ggcgatacag tctgggtcga tggtccactg acgcgcgccg ttcgagatgg cggcgtgtgt    300
tatctcgatg aagtggtcga ggcccgcaag gatgtcgctg tcgtgcttca cccgctgacc    360
gacgaccgcc gcattcttcc cttggagcgc accggtgaac agttggaagc gccaagctcg    420
tttatgctcg tcgtgtccta caatcccggt taccagagcc tgttgaagac actgaaacct    480
tccacccgcc agcgtttcgt ggcgatcgaa ttcgattttc tgcccaaggc gcgcgagatc    540
gaagtcgtgg cggaagaaag cggcctcgat gccgcgcgtg tcgaaccgct ggtcgaactt    600
gcccgccggc tgcgggcgct gaaaggccat gatctggaag agggtgtttc cacgcgtctt    660
ctggtttatt gcgccagcct gatcgacgcc ggcctgacc cgcgcgatgc cgttcgctcg    720
gcgatgatcg agcctctgac cgatgaagca ggatgtgcgc atcgcccttc tcgaactgat    780
gcagcggtga tccgctaa                                                  798

<210> SEQ ID NO 6
<211> LENGTH: 265
<212> TYPE: PRT
<213> ORGANISM: Pseudomonas sp. strain G-179

<400> SEQUENCE: 6

Met His Leu Arg His Ala Thr Ser Gln Ile Pro Ala Tyr Ala Pro Ala
 1               5                  10                  15
```

```
Gly Asn Glu Cys Ala Leu Phe Glu Thr Ala Trp Thr Arg Gln Leu Pro
             20                  25                  30

Leu Leu Leu Lys Gly Pro Thr Gly Cys Gly Lys Thr Arg Phe Val Gly
         35                  40                  45

His Met Ala Ala Lys Leu Gly Leu Pro Leu Ala Thr Val Ser Cys His
     50                  55                  60

Asp Asp Leu Ala Ala Ala Asp Leu Thr Gly Arg Tyr Leu Leu Lys Gly
 65                  70                  75                  80

Gly Asp Thr Val Trp Val Asp Gly Pro Leu Thr Arg Ala Val Arg Asp
                 85                  90                  95

Gly Gly Val Cys Tyr Leu Asp Glu Val Val Glu Ala Arg Lys Asp Val
             100                 105                 110

Ala Val Val Leu His Pro Leu Thr Asp Asp Arg Arg Ile Leu Pro Leu
         115                 120                 125

Glu Arg Thr Gly Glu Gln Leu Glu Ala Pro Ser Ser Phe Met Leu Val
     130                 135                 140

Val Ser Tyr Asn Pro Gly Tyr Gln Ser Leu Leu Lys Thr Leu Lys Pro
145                 150                 155                 160

Ser Thr Arg Gln Arg Phe Val Ala Ile Glu Phe Asp Phe Leu Pro Lys
                 165                 170                 175

Ala Arg Glu Ile Glu Val Val Ala Glu Glu Ser Gly Leu Asp Ala Ala
             180                 185                 190

Arg Val Glu Pro Leu Val Glu Leu Ala Arg Arg Leu Arg Ala Leu Lys
         195                 200                 205

Gly His Asp Leu Glu Glu Gly Val Ser Thr Arg Leu Leu Val Tyr Cys
     210                 215                 220

Ala Ser Leu Ile Asp Ala Gly Leu Asp Pro Arg Asp Ala Val Arg Ser
225                 230                 235                 240

Ala Met Ile Glu Pro Leu Thr Asp Glu Ala Gly Cys Ala His Arg Pro
                 245                 250                 255

Ser Arg Thr Asp Ala Ala Val Ile Arg
                 260                 265

<210> SEQ ID NO 7
<211> LENGTH: 1899
<212> TYPE: DNA
<213> ORGANISM: Pseudomonas sp. strain G-179

<400> SEQUENCE: 7
atgctggatt ttctcgaact cgaagaaact gtggggcgtg cctggcacaa ttttgctggc      60
aatacccgca catggccgcg gtatgaggcg gcggcggtga agctggagga ggtgcttccg     120
gtgatctccg tctgcttccg tggtttcggt ggtgagcgag cggtgcagct cgttccgcc     180 cggggcaagg catccgcgca tcgccttaaa cttcgacagc gcgtggggct gggcgaggaa     240
aaactcgtcc agcccgcccg cgacgaggca tcgctgatgt tgccgccggt gctcgacctg     300
atgccggagc gtgatctcaa ccgtgatctt tatctctggc tggcggcgat catggcgcgg     360
atggaccttg tcccgatcca tgaaaccgat ccgcttcggc gcgatctcgc cctgctcgaa     420
caggcggcgc gccgggtgga agatgtgctc gagacctttc cgggcttggc gccgcggtat     480
caaaatctct ggcctgtcgc tgatcgaaca acggcagcgcg gaaagctgcc acgtatcgag     540
cagatggtgg aaaaccgcat cggcgatctg ttgcggcatg cgccggtct tgcgcccttg     600 tacaaggcgg gtccgtggcc gctgaaggca ccacccggtt atctgccgat gctgccggtg     660
ccgctttggc cagatgcgtt gtcacgtgag gaggcagaac cgcggcagga ggaggatcgt     720
```

-continued

```
ccggccggtg gcgcatcgca ggaagccatg gcgggtggcc gccacattgc cgtgcgcgaa      780
aaggattctc aaaggaaagg cgagcgcagc ccgttcattc tcaaccggtt cgaaaaaatc      840
ctcgccatgg cggagatggt caatgtcgac cggcccggcg acgacagcga cgatcatgac      900
gcggcggcgg ccgacgaact ggacgagatg acgctcggcg agcgccaagg cggccatcg       960 gcaaaattcc gcttcgatct cgacctgccg ccggaagcac tggtgcataa gccttttgtc     1020
gccgaactca cctatcccga atgggattat cgtcgcggta tctatctgcg cgatcattgc     1080
cgggtgtttg ccggtccggc accactggag ggcgaggatt ccagcagtc cgaagaggtg     1140 aaaaacctca ttcgccgggt gcggcggcag ttcgaggtga tgcggccgaa cgcgaaatg      1200 ctgcgcgccc agtcgatgg ttcagatctc gatctcgatg ccgttgtgcg cagccgtacc     1260
gatctgaaag cgagcggcga atgctccgac cgcattcatc tgatgagccg gccgcaggcg     1320
catgatctgg cggtgacgct tctggtcgat gtgtcgcttt cgacggattc ctggttcaat     1380
gaccggcgcg tgctcgatgt cgagaaagaa gcgctgatgg tgctggcgga aggtcttct     1440 gcctgcggtg acaaccattc aatcctcacc ttcacctcgc ggcgtcgcga ctgggtgcgg     1500
gtggaaacca tcaaggcgtt cgatgagccg atgagccatg cggtgcgccg ccgtatcgcc     1560
tcgctgaagc cgggttatta tacccgcatc ggcgctgcga tccgtcatgc cgcggcaaaa     1620
ctgtccgaac agccgaaccg caaacatctg atgctggtgc tgaccgacgg caagcccaat     1680
gatgtcgatc attatgaagg ccggtttgcg ctggaggata cccgtcgttc ggtgatcgag     1740
gcgcgtcgca agggtgtgca ggtgttcggc gttaccgtcg accaggatgc caaatcctat     1800
gtgccggcaa tgttcggcca gcatggattt gctgtcgtgc ccgacatccg caaactgcct     1860
tcggcgcttc cggccatcta tcgcgggctg gtcggttaa                            1899
```

<210> SEQ ID NO 8
<211> LENGTH: 632
<212> TYPE: PRT
<213> ORGANISM: Pseudomonas sp. strain G-179

<400> SEQUENCE: 8

```
Met Leu Asp Phe Leu Glu Leu Glu Glu Thr Val Gly Arg Ala Trp His
 1               5                  10                  15

Asn Phe Ala Gly Asn Thr Arg Thr Trp Pro Arg Tyr Glu Ala Ala Ala
                20                  25                  30

Val Lys Leu Glu Glu Val Leu Pro Val Ile Ser Val Cys Phe Arg Gly
            35                  40                  45

Phe Gly Gly Glu Arg Ala Val Gln Leu Val Pro Ala Arg Gly Lys Ala
        50                  55                  60

Ser Ala His Arg Leu Lys Leu Arg Gln Arg Val Gly Leu Gly Glu Glu
 65                  70                  75                  80

Lys Leu Val Gln Pro Ala Arg Asp Glu Ala Ser Leu Met Leu Pro Pro
                85                  90                  95

Val Leu Asp Leu Met Pro Glu Arg Asp Leu Asn Arg Asp Leu Tyr Leu
            100                 105                 110

Trp Leu Ala Ala Ile Met Ala Arg Met Asp Leu Val Pro Ile His Glu
        115                 120                 125

Thr Asp Pro Leu Arg Arg Asp Leu Ala Leu Leu Glu Gln Ala Ala Arg
    130                 135                 140

Arg Val Glu Asp Val Leu Glu Thr Phe Pro Gly Leu Ala Pro Arg Tyr
145                 150                 155                 160
```

-continued

```
Gln Asn Leu Cys Leu Ser Leu Ile Glu Gln Arg Gln Arg Gly Lys Leu
                165                 170                 175

Pro Arg Ile Glu Gln Met Val Glu Asn Arg Ile Gly Asp Leu Leu Arg
            180                 185                 190

His Gly Ala Gly Leu Ala Pro Leu Tyr Lys Ala Gly Pro Trp Pro Leu
        195                 200                 205

Lys Ala Pro Pro Gly Tyr Leu Pro Met Leu Pro Val Pro Leu Trp Pro
    210                 215                 220

Asp Ala Leu Ser Arg Glu Glu Ala Glu Pro Arg Gln Glu Glu Asp Arg
225                 230                 235                 240

Pro Ala Gly Gly Ala Ser Gln Glu Ala Met Ala Gly Gly Arg His Ile
                245                 250                 255

Ala Val Arg Glu Lys Asp Ser Gln Arg Lys Gly Glu Arg Ser Pro Phe
            260                 265                 270

Ile Leu Asn Arg Phe Glu Lys Ile Leu Ala Met Ala Glu Met Val Asn
        275                 280                 285

Val Asp Arg Pro Gly Asp Asp Ser Asp Asp His Asp Ala Ala Ala Ala
    290                 295                 300

Asp Glu Leu Asp Glu Met Thr Leu Gly Glu Arg Gln Gly Arg Pro Ser
305                 310                 315                 320

Ala Lys Phe Arg Phe Asp Leu Asp Leu Pro Pro Glu Ala Leu Val His
                325                 330                 335

Lys Pro Phe Val Ala Glu Leu Thr Tyr Pro Glu Trp Asp Tyr Arg Arg
            340                 345                 350

Gly Ile Tyr Leu Arg Asp His Cys Arg Val Phe Ala Gly Pro Ala Pro
        355                 360                 365

Leu Glu Gly Glu Asp Phe Gln Gln Ser Glu Glu Val Lys Asn Leu Ile
    370                 375                 380

Arg Arg Val Arg Arg Gln Phe Glu Val Met Arg Pro Lys Arg Glu Met
385                 390                 395                 400

Leu Arg Ala Gln Phe Asp Gly Ser Asp Leu Asp Leu Asp Ala Val Val
                405                 410                 415

Arg Ser Arg Thr Asp Leu Lys Ala Ser Gly Glu Cys Ser Asp Arg Ile
            420                 425                 430

His Leu Met Ser Arg Pro Gln Ala His Asp Leu Ala Val Thr Leu Leu
        435                 440                 445

Val Asp Val Ser Leu Ser Thr Asp Ser Trp Phe Asn Asp Arg Arg Val
    450                 455                 460

Leu Asp Val Glu Lys Glu Ala Leu Met Val Leu Ala Glu Gly Leu Ser
465                 470                 475                 480

Ala Cys Gly Asp Asn His Ser Ile Leu Thr Phe Thr Ser Arg Arg Arg
                485                 490                 495

Asp Trp Val Arg Val Glu Thr Ile Lys Ala Phe Asp Glu Pro Met Ser
            500                 505                 510

His Ala Val Arg Arg Ile Ala Ser Leu Lys Pro Gly Tyr Tyr Thr
        515                 520                 525

Arg Ile Gly Ala Ala Ile Arg His Ala Ala Lys Leu Ser Glu Gln
    530                 535                 540

Pro Asn Arg Lys His Leu Met Leu Val Leu Thr Asp Gly Lys Pro Asn
545                 550                 555                 560

Asp Val Asp His Tyr Glu Gly Arg Phe Ala Leu Glu Asp Thr Arg Arg
                565                 570                 575

Ser Val Ile Glu Ala Arg Arg Lys Gly Val Gln Val Phe Gly Val Thr
```

|  |  | 580 |  |  |  | 585 |  |  |  | 590 |  |
|--|--|--|--|--|--|--|--|--|--|--|--|

Val Asp Gln Asp Ala Lys Ser Tyr Val Pro Ala Met Phe Gly Gln His
             595                 600             605

Gly Phe Ala Val Val Pro Asp Ile Arg Lys Leu Pro Ser Ala Leu Pro
    610                 615                 620

Ala Ile Tyr Arg Gly Leu Val Gly
625             630

<210> SEQ ID NO 9
<211> LENGTH: 2505
<212> TYPE: DNA
<213> ORGANISM: Pseudomonas sp. strain G-179

<400> SEQUENCE: 9

```
atgacggcag aactcacgcg gcgtgatgtg ctgaaggcac aggcggctgc gatcgcggct     60
tcgacagccg gcatcgccat gccggcagcc gcccaatccg tccccggtgg cgtcgcggcg    120
ctggaaatca agtggtccaa ggcgccctgt cgcttctgcg gcaccggctg cggtgtcatg    180
gtcggcgtca aggaaaacca cgtcgtcgcg acccatggcg acatggaagc agaggtcaat    240
cgcggcctga actgtgtcaa aggctacttc ctctcgaaga tcatgtacgg caaggaccgt    300
ctgaccacgc cgctcctgcg caagcgcaac ggcgtgttcg acaaggaagg tgaattcgaa    360
cccgtcacct gggaagaagc cttcgacatt atggccgaaa aggccaagaa gaccctgaag    420
gaaaaaggtc cgacggcgct tggcatgttc ggctccggcc agtggaccat tttcgaaggc    480
tatgccgcga caaaactgat gcgcgccggc ttccgttcca caatctcga ccccaatgcc    540
cgccactgca tggcatcggc ggcctacggc ttcatgcgca cgttcggcat ggacgagccg    600
atgggctgtt atgacgattt cgagcatgcc gacgctttcg tgctgtgggg ctcgaacatg    660
gcggagatgc acccgatcct gtggacgcgc cttgccgatc gtcgcctcgg ccatgagcat    720
gtgaaggtct cggtactttc gaccttcacc catcgcagca tggacctggc cgacattccg    780
ctggtcttca gcccggcac ggatctggcg atcctcaact atatcgccaa ccacatcatt    840
cagaccggtc gcgtgaacca ggaattcatc gacaagaaca ccaagttcat gcaggcaacg    900
accgatatcg gttatggcct gcgcgccgaa catccgctgg aggtcaaggc aaccggcgcg    960
gccaaggccg ccgagatgac gccgatcgat ttcgaggcct tcaagaaaca cgtttcggaa   1020
tacacgctcg aaaaagttgc cgaactggcc ggtgtcgaca aagggtttct ggaacagctg   1080
gcagaattgt acgccgaccc caaagtcaag gtcatgtcgc tctggaccat gggcttcaac   1140
cagcacgtcc gaggcgtctg gccaaccag atggtctaca atatccatct cttgaccggc   1200
aaaatctccg agccgggcaa tagcccttc tcactgaccg ccagccttc ggcctgcggc    1260
accgcccgcg aggtcggcac gttcgcacac cgtctgccgg cagacatgac ggtaaccaat   1320
ccggaacacc gcaagcatgc agaggaattg tggaacatcc gcacggcat cattccggaa    1380
aagccgggtt accatgccgt ccagcaggat cgcatgctgc atgatggcaa gctgaacttc   1440
tactgggttc aggtgaacaa caacatgcag gccgctgcca caacagcaa cgaggcctat   1500
atcggatacc gcaacccgga caacttcatc gtcgtctcgg atgcctatcc gacggtgacc   1560
gcgatgaccg ccgacctgat cctgcccgcc gcgatgtggg tggaaaagga aggcgcttac   1620
ggcaatgccg aacgccgcac ccatgtctgg caccaactgg tcaacgcgcc gggcgaagcc   1680
cgctccgacc tctggcagct tgttgaattc ccaagcgct tcacgaccga tgaagtctgg   1740
ccgcaggaca ttctcgacca gaacccggag tacaaggaa aaaccctgta tgacgtgctc    1800
```

```
ttccagaatg gcaatgtcga caagttcccg gtctccgaaa tctcgtcgga ttatgagaac    1860
cgcgaagcga aggctttcgg cttctacctg cagaagggcc tgttcgagga atatgccagc    1920
ttcggccgtg gtcacggcca tgaccttggc ccgtacgacc tctaccacca ggttcgcggc    1980
ctgcgctggc cggtcgtcaa caaccaggag accaagtggc gttaccgcga aggttacgat    2040
ccctatgtga aggaaggcga aggcgtcaaa ttttacggcc agaacgatgg ccgcgccgtc    2100
atcctcgcag cgccctacga gccaccggca gaatcgccgg atgacgaatt cggcttctgg    2160
ctggtcaccg gccgcgttct cgaacactgg cattccggct ccatgaccat gcgggtgccg    2220
gaactctaca aggcatttcc gggtgcccgc tgcttcatga acggcgacga cgcacgccgc    2280
ctcggcatca atcagggcgg acaggtgaaa atccagtccc gccgtggcga gatcatcagc    2340
cgggtggata tccgcgggcg aaaccgcatg ccgcatggcg tgatcttcgt gccgtggttc    2400
gacgccagcc agctcatcaa caaggtcacg ctcgacgcca ccgacccat ttccaaacag    2460 acggatttca aaaatgcgc agtcaagatc cttcccgtcg cctga                    2505
```

<210> SEQ ID NO 10
<211> LENGTH: 853
<212> TYPE: PRT
<213> ORGANISM: Pseudomonas sp. strain G-179

<400> SEQUENCE: 10

```
Met Ser Ser Pro His Thr Trp Phe Ser Asn Arg Gln Leu Gln Lys Arg
  1               5                  10                  15

Arg Cys Arg Met Thr Ala Glu Leu Thr Arg Arg Asp Val Leu Lys Ala
                 20                  25                  30

Gln Ala Ala Ile Ala Ala Ser Thr Ala Gly Ile Ala Met Pro Ala
         35                  40                  45

Ala Ala Gln Ser Val Pro Gly Gly Val Ala Ala Leu Glu Ile Lys Trp
     50                  55                  60

Ser Lys Ala Pro Cys Arg Phe Cys Gly Thr Gly Cys Gly Val Met Val
 65                  70                  75                  80

Gly Val Lys Glu Asn His Val Val Ala Thr His Gly Asp Met Glu Ala
                 85                  90                  95

Glu Val Asn Arg Gly Leu Asn Cys Val Lys Gly Tyr Phe Leu Ser Lys
                100                 105                 110

Ile Met Tyr Gly Lys Asp Arg Leu Thr Thr Pro Leu Leu Arg Lys Arg
            115                 120                 125

Asn Gly Val Phe Asp Lys Glu Gly Glu Phe Glu Pro Val Thr Trp Glu
        130                 135                 140

Glu Ala Phe Asp Ile Met Ala Glu Lys Ala Lys Lys Thr Leu Lys Glu
145                 150                 155                 160

Lys Gly Pro Thr Ala Leu Gly Met Phe Gly Ser Gly Gln Trp Thr Ile
                165                 170                 175

Phe Glu Gly Tyr Ala Ala Thr Lys Leu Met Arg Ala Gly Phe Arg Ser
            180                 185                 190

Asn Asn Leu Asp Pro Asn Ala Arg His Cys Met Ala Ser Ala Ala Tyr
        195                 200                 205

Gly Phe Met Arg Thr Phe Gly Met Asp Glu Pro Met Gly Cys Tyr Asp
    210                 215                 220

Asp Phe Glu His Ala Asp Ala Phe Val Leu Trp Gly Ser Asn Met Ala
225                 230                 235                 240

Glu Met His Pro Ile Leu Trp Thr Arg Leu Ala Asp Arg Arg Leu Gly
                245                 250                 255
```

-continued

```
His Glu His Val Lys Val Ser Val Leu Ser Thr Phe Thr His Arg Ser
            260                 265                 270

Met Asp Leu Ala Asp Ile Pro Leu Val Phe Lys Pro Gly Thr Asp Leu
            275                 280                 285

Ala Ile Leu Asn Tyr Ile Ala Asn His Ile Ile Gln Thr Gly Arg Val
            290                 295                 300

Asn Gln Glu Phe Ile Asp Lys Asn Thr Lys Phe Met Gln Ala Thr Thr
305                 310                 315                 320

Asp Ile Gly Tyr Gly Leu Arg Ala Glu His Pro Leu Glu Val Lys Ala
                325                 330                 335

Thr Gly Ala Ala Lys Ala Ala Glu Met Thr Pro Ile Asp Phe Glu Ala
            340                 345                 350

Phe Lys Lys His Val Ser Glu Tyr Thr Leu Glu Lys Val Ala Glu Leu
            355                 360                 365

Ala Gly Val Asp Lys Gly Phe Leu Glu Gln Leu Ala Glu Leu Tyr Ala
            370                 375                 380

Asp Pro Lys Val Lys Val Met Ser Leu Trp Thr Met Gly Phe Asn Gln
385                 390                 395                 400

His Val Arg Gly Val Trp Ala Asn Gln Met Val Tyr Asn Ile His Leu
                405                 410                 415

Leu Thr Gly Lys Ile Ser Glu Pro Gly Asn Ser Pro Phe Ser Leu Thr
            420                 425                 430

Gly Gln Pro Ser Ala Cys Gly Thr Ala Arg Glu Val Gly Thr Phe Ala
            435                 440                 445

His Arg Leu Pro Ala Asp Met Thr Val Thr Asn Pro Glu His Arg Lys
            450                 455                 460

His Ala Glu Glu Leu Trp Asn Ile Pro His Gly Ile Ile Pro Glu Lys
465                 470                 475                 480

Pro Gly Tyr His Ala Val Gln Gln Asp Arg Met Leu His Asp Gly Lys
                485                 490                 495

Leu Asn Phe Tyr Trp Val Gln Val Asn Asn Asn Met Gln Ala Ala Ala
            500                 505                 510

Asn Asn Ser Asn Glu Ala Tyr Ile Gly Tyr Arg Asn Pro Asp Asn Phe
            515                 520                 525

Ile Val Val Ser Asp Ala Tyr Pro Thr Val Thr Ala Met Thr Ala Asp
            530                 535                 540

Leu Ile Leu Pro Ala Ala Met Trp Val Glu Lys Glu Gly Ala Tyr Gly
545                 550                 555                 560

Asn Ala Glu Arg Arg Thr His Val Trp His Gln Leu Val Asn Ala Pro
                565                 570                 575

Gly Glu Ala Arg Ser Asp Leu Trp Gln Leu Val Glu Phe Ser Lys Arg
            580                 585                 590

Phe Thr Thr Asp Glu Val Trp Pro Gln Asp Ile Leu Asp Gln Asn Pro
            595                 600                 605

Glu Tyr Lys Gly Lys Thr Leu Tyr Asp Val Leu Phe Gln Asn Gly Asn
            610                 615                 620

Val Asp Lys Phe Pro Val Ser Glu Ile Ser Ser Asp Tyr Glu Asn Arg
625                 630                 635                 640

Glu Ala Lys Ala Phe Gly Phe Tyr Leu Gln Lys Gly Leu Phe Glu Glu
                645                 650                 655

Tyr Ala Ser Phe Gly Arg Gly His Gly His Asp Leu Gly Pro Tyr Asp
            660                 665                 670
```

```
Leu Tyr His Gln Val Arg Gly Leu Arg Trp Pro Val Val Asn Asn Gln
            675                 680                 685

Glu Thr Lys Trp Arg Tyr Arg Glu Gly Tyr Asp Pro Tyr Val Lys Glu
        690                 695                 700

Gly Glu Gly Val Lys Phe Tyr Gly Gln Asn Asp Gly Arg Ala Val Ile
705                 710                 715                 720

Leu Ala Ala Pro Tyr Glu Pro Pro Ala Glu Ser Pro Asp Asp Glu Phe
                725                 730                 735

Gly Phe Trp Leu Val Thr Gly Arg Val Leu Glu His Trp His Ser Gly
            740                 745                 750

Ser Met Thr Met Arg Val Pro Glu Leu Tyr Lys Ala Phe Pro Gly Ala
        755                 760                 765

Arg Cys Phe Met Asn Gly Asp Asp Ala Arg Arg Leu Gly Ile Asn Gln
    770                 775                 780

Gly Gly Gln Val Lys Ile Gln Ser Arg Arg Gly Glu Ile Ile Ser Arg
785                 790                 795                 800

Val Asp Ile Arg Gly Arg Asn Arg Met Pro His Gly Val Ile Phe Val
                805                 810                 815

Pro Trp Phe Asp Ala Ser Gln Leu Ile Asn Lys Val Thr Leu Asp Ala
            820                 825                 830

Thr Asp Pro Ile Ser Lys Gln Thr Asp Phe Lys Lys Cys Ala Val Lys
        835                 840                 845

Ile Leu Pro Val Ala
    850

<210> SEQ ID NO 11
<211> LENGTH: 492
<212> TYPE: DNA
<213> ORGANISM: Pseudomonas sp. strain G-179

<400> SEQUENCE: 11
atgcgcagtc aagatccttc ccgtcgcctg agccggcgtc tctggacgct tttcgcgctt    60
gctctgtgtc tggtcaccgg cacggtcgcc cttgcgcaaa cggtgccgca attgtcgggc   120
cgtccaagcc cgatgcaaaa caccggtgcg gatccgctgc gagatggat cgtcgatgac   180 atccagaaga tgcgcaacta tccggaccag ccgcccgtca tcccgcattc gatcgagggc   240
taccagctgt cggtcaacac caatcgctgc atgtcctgtc accggcgtga actcaccgaa   300
ggttccggcg cgccgatgat cagcgttacc cattacatga accgtgaggg ccagatgctc   360
gccgacgttt cgccacgccg ttatttctgc acggcatgcc acgtaccgca ggccgataca   420
cggccactgg tcgacaacac gttcaaggac atgagcgaac tcggcttcaa accggcagga   480
tctggacaat ga                                                       492

<210> SEQ ID NO 12
<211> LENGTH: 163
<212> TYPE: PRT
<213> ORGANISM: Pseudomonas sp. strain G-179

<400> SEQUENCE: 12

Met Arg Ser Gln Asp Pro Ser Arg Arg Leu Ser Arg Arg Leu Trp Thr
1               5                   10                  15

Leu Phe Ala Leu Ala Leu Cys Leu Val Thr Gly Thr Val Ala Leu Ala
            20                  25                  30

Gln Thr Val Pro Gln Leu Ser Gly Arg Pro Ser Pro Met Gln Asn Thr
        35                  40                  45
```

Gly Ala Asp Pro Leu Pro Arg Trp Ile Val Asp Ile Gln Lys Met
        50                  55                  60

Arg Asn Tyr Pro Asp Gln Pro Val Ile Pro His Ser Ile Glu Gly
 65                  70                  75                  80

Tyr Gln Leu Ser Val Asn Thr Asn Arg Cys Met Ser Cys His Arg Arg
                85                  90                  95

Glu Leu Thr Glu Gly Ser Gly Ala Pro Met Ile Ser Val Thr His Tyr
            100                 105                 110

Met Asn Arg Glu Gly Gln Met Leu Ala Asp Val Ser Pro Arg Arg Tyr
            115                 120                 125

Phe Cys Thr Ala Cys His Val Pro Gln Ala Asp Thr Arg Pro Leu Val
        130                 135                 140

Asp Asn Thr Phe Lys Asp Met Ser Glu Leu Gly Phe Lys Pro Ala Gly
145                 150                 155                 160

Ser Gly Gln

<210> SEQ ID NO 13
<211> LENGTH: 705
<212> TYPE: DNA
<213> ORGANISM: Pseudomonas sp. strain G-179

<400> SEQUENCE: 13
atgatcggca tgatcaaagc agtgatcctc tgggcctggc gtattctcgc cacgcccgct     60
ggaaccttgg gcctcgggtt tctgacactt ggcggttttg tcggaggagt gattttctgg    120
ggggcgttca acacggcgct ggaagtgacc aataccgagg ccttctgtac cggctgtcat    180
gaaatgaaga caaacgtcta cgaggaattg acgcagacgg tgcatttctc caaccgttcg    240
ggtgttcggg catcctgccc ggattgccac gttccgcatc aatggaccga caagatcgcc    300
cgcaagatgc aggcttcgaa ggaggtgtgg ggcaagatct tcggcacgat cagcacgcgc    360
gagaaatttc tcgacaagcg gcttgagctt gcccagcacg aatgggcgcg tctgaaggcc    420
aatgacagcc tggaatgccg gaactgccac tcgtcgattg cgatggattt gaccaagcag    480
acgaaacgcg ccgccgacat tcacacacgt tatctcctct ccggcaaagc gacctgtatc    540
gattgccata aggcatcgc gcatgaactt cccaacatgg atggtgtcga tccgggctgg    600
aaggttccgg ccgaactgat gggcaaggcc gcctcgcacg gccttcagga tacggatcag    660
ctggcagcct atctggccgc ccgggaaggt aacatcatcg actga                     705

<210> SEQ ID NO 14
<211> LENGTH: 234
<212> TYPE: PRT
<213> ORGANISM: Pseudomonas sp. strain G-179

<400> SEQUENCE: 14

Met Ile Gly Met Ile Lys Ala Val Ile Leu Trp Ala Trp Arg Ile Leu
 1               5                  10                  15

Ala Thr Pro Ala Gly Thr Leu Gly Leu Gly Phe Leu Thr Leu Gly Gly
                20                  25                  30

Phe Val Gly Gly Val Ile Phe Trp Gly Ala Phe Asn Thr Ala Leu Glu
            35                  40                  45

Val Thr Asn Thr Glu Ala Phe Cys Thr Gly Cys His Glu Met Lys Thr
        50                  55                  60

Asn Val Tyr Glu Glu Leu Thr Gln Thr Val His Phe Ser Asn Arg Ser
 65                  70                  75                  80

Gly Val Arg Ala Ser Cys Pro Asp Cys His Val Pro His Gln Trp Thr

```
                        85                      90                      95
Asp Lys Ile Ala Arg Lys Met Gln Ala Ser Lys Glu Val Trp Gly Lys
                100                 105                 110
Ile Phe Gly Thr Ile Ser Thr Arg Glu Lys Phe Leu Asp Lys Arg Leu
        115                 120                 125
Glu Leu Ala Gln His Glu Trp Ala Arg Leu Lys Ala Asn Asp Ser Leu
        130                 135                 140
Glu Cys Arg Asn Cys His Ser Ser Ile Ala Met Asp Leu Thr Lys Gln
145                 150                 155                 160
Thr Lys Arg Ala Ala Asp Ile His Thr Arg Tyr Leu Leu Ser Gly Lys
                165                 170                 175
Ala Thr Cys Ile Asp Cys His Lys Gly Ile Ala His Glu Leu Pro Asn
                180                 185                 190
Met Asp Gly Val Asp Pro Gly Trp Lys Val Pro Ala Glu Leu Met Gly
        195                 200                 205
Lys Ala Ala Ser His Gly Leu Gln Asp Thr Asp Gln Leu Ala Ala Tyr
        210                 215                 220
Leu Ala Ala Arg Glu Gly Asn Ile Ile Asp
225                 230
```

GENES ENCODING DENITRIFICATION ENZYMES

Figure 1:
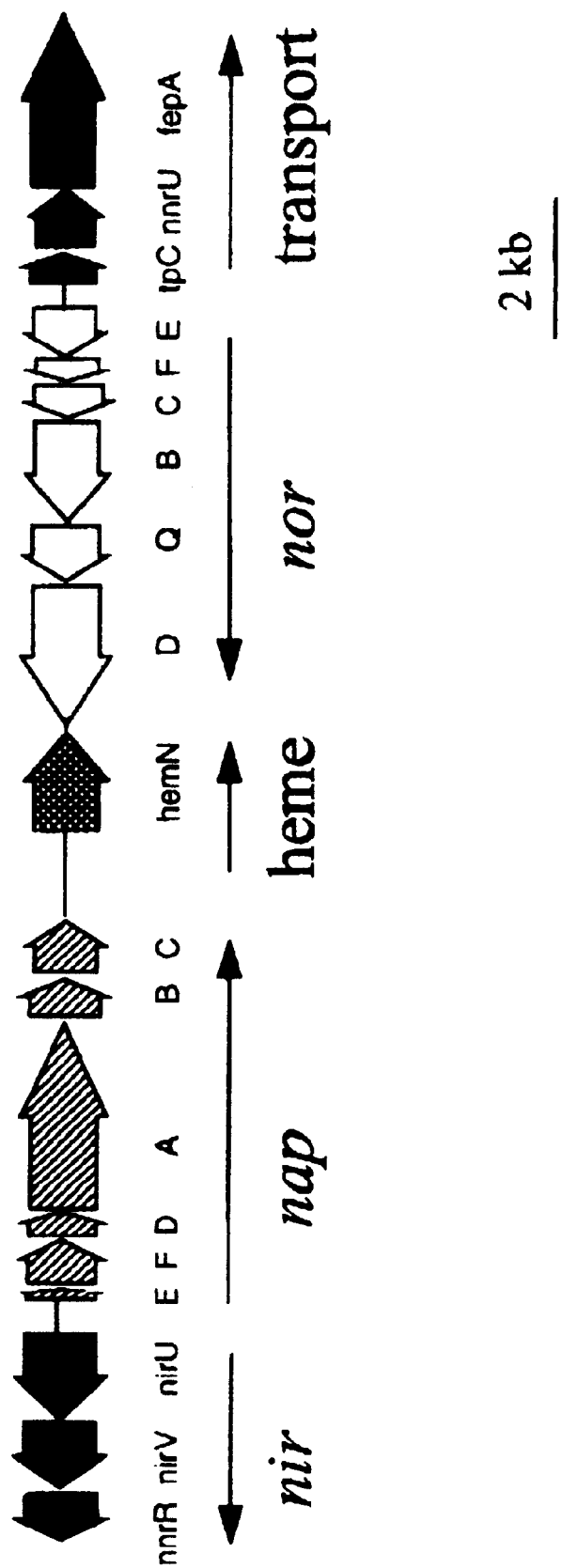

This is a Divisional application, filed under 37C.F.R. 1.153(b) and claiming priority to U.S. Ser. No. 09/354,129, filed Jul. 15, 1999 which issued as U.S. Pat. No. 6,136,583 which claims priority to U.S. Ser. No. 60/093,191, filed Jul. 17, 1998 now abandoned.

FIELD OF THE INVENTION

This invention is in the field of microbial denitrification. More specifically, this invention pertains to nucleic acid fragments encoding new bacterial nitric oxide reductase and bacterial periplasmic nitrate reductase enzymes.

BACKGROUND OF THE INVENTION

The complete pathway for microbial denitrification has been established as:

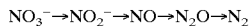

(Ye et al., *Appl. Environ. Microbiol.* 60:1053–1058 (1994); Zumft et al., *Microbiol. Mol. Biol. Rev.* 61:533–616 (1997)). In the natural environment, denitrification plays a major role in completing the nitrogen cycle by converting nitrate ($NO_3^-$) or nitrite ($NO_2^-$) to nitrogen gas ($N_2$). Bacteria attempt to maintain the balance necessary between fixed nitrogen and atmospheric nitrogen. In the denitrification process, the soil bacteria use nitrate, rather than oxygen, as the ultimate electron acceptor in a series of reactions to generate a transmembrane proton gradient that is used to synthesize ATP.

In practical applications, microbial denitrification has been widely used for water purification (Mateju et al., *Enzyme Microb. Technol.* 14:172–183 (1992)). On the other hand, nitrous oxide ($N_2O$) has been shown to have detrimental effect on the stratospheric ozone layer (de Boer et al., *Eur. J. Biochem.* 242:592–600 (1996)). NOx, along with carbon monoxide and hydrocarbons can lead to an increase in the amount of stratospheric ozone. Thus, the production of $N_2O$ and nitric oxide (NO) due to incomplete denitrification is of concern. It will be useful therefore to devise new and better methods for denitrification of industrial waste streams to effect complete denitrification. The identification of genes encoding proteins responsible for key denitrification reactions will be essential for the development of improved denitrification methods.

Two of the essential genes in the bacterial denitrification pathway are those encoding nitric oxide reductase (nor) and nitrate reductase (nap). Genes encoding these enzymes have been identified in both denitrifying bacteria as well as non-denitryfers. For example, Bartnikas et al., *J. Bacteriol.* 179:3534–3540 (1997) teach the identification and sequencing of a gene cluster required for the expression of nitric oxide reductase in *Rhodobacter sphaeroidesi* and de Boer et al., (*Eur. J. Biochem.* 242:592–600 (1996)) describe a nor gene cluster isolated from *Paracoccus denitrificans*. Genes encoding periplasmic nitrate reductase have been characterized from *Thiosphaera pantotropha* (Berks et al., *Biochem J.*, (1995), 309, 983) and from *Rhodobacter sphaeroides* (Reyes et al., *Biochem J.*, (1998), 331, 897). Finally Grove et al., (*Mol. Microbiol.* 19:467–481 (1996)) describe the identification of a gene encoding a periplasmic nitrate reductase from the non-denitrifying *E. coli* K-12.

The utility in being able to manipulate the nor and nap genes to modify bacterial denitrification is clear from the interplay of these enzymes with the genes encoding nitrite reductase (nir) in the bacterial denitrification process. In bacterial denitrification, NO is produced from $NO_3^-$ in two consecutive reactions catalyzed by the two metalloenzymes nitrate reductase and nitrite reductase, and then is decomposed into $N_2O$ by nitric oxide reductase. The key step of denitrification is the reduction of $NO_2^-$ by nitrite reductases. These quintessential enzymes catalyze the conversion of a mineral form of nitrogen to a gaseous form. It is well recognized that gaseous forms of nitrogen compounds are no longer easily available for assimilation by the biomass.

The product of nitrite reduction, NO, is only present in trace amount due to its efficient removal by nitric oxide reductase. However, it has been observed that mutations in the NO step render the cells incapable of using nitrate and nitrite as the alternative electron acceptors due to NO toxicity. In addition, mutations in the nitric oxide reductase (nor) region have shown a negative impact on the activity or expression level of nitrite reductase (nir) in *Pseudomonas stutzeri* and *Paracoccus denitrificans* (Grove et al., *Mol. Microbiol.* 19:467–481 (1996); Zumft et al., *Eur. J. Biochem.* 219:481–490 (1994)). Nonetheless, in *Rhodobacter sphaeroides*, promoter activity for the nitrite reductase gene nirK was higher in nor mutants (Bartnikas et al., *J. Bacteriol.* 179:3534–3540 (1997)). Activities of these two steps are commonly controlled by the proteins NnrU, NirQ, and NnrR (Bell et al., *FEBS Lett.* 265:85–87 (1990); Kastrau et al., *Eur. J. Biochem.* 222:293–303 (1994); Tyson et al., *Arch. Microbiol.* 168:403–411 (1997)), depending on the organism studied. This evidence distinctly suggests that reduction of nitrite and nitric oxide is highly interdependent.

Prior to the identification of role of the nitrate reductases in the periplasmic space, the principal nitrate reductase activity in bacterial denitrification has been attributed to those associated with membrane (Bell et al, 1993, *J. of General Microbiology*, Vol. 139, p. 3205–3214).

Applicant has discovered new genes isolated from Pseudomonas sp. encoding a periplasmic nitrate reductase and nitric oxide reductase. The genes are may be expressed in recombinant systems effect bacterial denitrification and the genes or portions thereof may be used to identify other denitrifying bacterial strains. Further, it has been demonstrate that the instant periplasmic nitrate reductase is the penultimate nitrate reductase in the denitrification pathway as compared with the cytoplasmic variety of the enzyme in Pseudomonas sp.

SUMMARY OF THE INVENTION

This invention relates to isolated nucleic acid fragments encoding a bacterial nitric oxide reductase selected from the group consisting of: (a) an isolated nucleic acid fragment encoding all or a substantial portion of the amino acid sequence selected from the group consisting of SEQ ID NO:2, SEQ ID NO:4, SEQ ID NO:6 and SEQ ID NO:8; (b) an isolated nucleic acid fragment that is substantially similar to an isolated nucleic acid fragment encoding all or a substantial portion of the amino acid sequence selected from the group consisting of SEQ ID NO:2, SEQ ID NO:4, SEQ ID NO:6 and SEQ ID NO:8; (c) an isolated nucleic acid fragment encoding a polypeptide having at least a 73% identity with the amino acid sequence selected from the group consisting of SEQ ID NO:2, SEQ ID NO:4, SEQ ID NO:6 and SEQ ID NO:8; (d) an isolated nucleic acid molecule that hybridizes with SEQ ID NO:1, SEQ ID NO:3, SEQ ID NO:5 or SEQ ID NO:7 under the following hybridization conditions: 40% formamide, with 5× or 6×SSC; and (e) an isolated nucleic acid fragment that is complementary to (a), (b), (c) or (d).

The present invention further provides isolated nucleic acid fragments encoding a bacterial periplasmic nitrate reductase selected from the group consisting of: (a) an isolated nucleic acid fragment encoding all or a substantial portion of the amino acid sequence selected from the group consisting of SEQ ID NO:10, SEQ ID NO:12 and SEQ ID NO:14; (b) an isolated nucleic acid fragment that is substantially similar to an isolated nucleic acid fragment encoding all or a substantial portion of the amino acid sequence selected from the group consisting of SEQ ID NO:10, SEQ ID NO:12 and SEQ ID NO:14; (c) an isolated nucleic acid fragment encoding a polypeptide having at least a 76% identity with the amino acid sequence selected from the group consisting of SEQ ID NO:10, SEQ ID NO:12 and SEQ ID NO:14; (d) an isolated nucleic acid molecule that hybridizes with SEQ ID NO:9, SEQ ID NO:11 or SEQ ID NO:13 under the following hybridization conditions: 40% formamide, with 5× or 6×SSC.; and (e) an isolated nucleic acid fragment that is complementary to (a), (b), (c) or (d).

In another embodiment, the instant invention relates to chimeric genes encoding a bacterial nitric oxide reductase or bacterial periplasmic nitrate reductase or to chimeric genes that comprise nucleic acid fragments as described above, the chimeric genes operably linked to suitable regulatory sequences, wherein expression of the chimeric genes results in transformation of the respective enzyme substrates.

The present invention further provides a transformed host cell comprising the above described chimeric genes. The transformed host cells can be of eucaryotic or procaryotic origin.

In an alternate embodiment, the present invention provides methods of obtaining a nucleic acid fragment encoding all or substantially all of the amino acid sequence encoding a bacterial nitric oxide reductase comprising either hybridization or primer-directed amplification methods known in the art and using the above described nucleic acid fragment. Primer-directed amplification methods use all or a part of SEQ ID NO:1, SEQ ID NO:3, SEQ ID NO:5 and SEQ ID NO:7. The product of these methods is also provided by the invention.

Similarly, the invention provides methods of obtaining a nucleic acid fragment encoding all or substantially all of the amino acid sequence encoding a bacterial periplasmic nitrate reductase comprising either hybridization or primer-directed amplification methods known in the art and using the above described nucleic acid fragments. Primer-directed amplification methods use all of a part of SEQ ID NO:9, SEQ ID NO:11 and SEQ ID NO:13. The product of these methods is also provided by the invention.

Finally the invention provides methods for bacterial denitrification incorporating recombinant hosts expressing the present nitrate reductase and nitric oxide reductase enzymes.

BRIEF DESCRIPTION OF THE DRAWINGS, SEQUENCE DESCRIPTIONS

FIG. 1 is a diagram showing the confirmation of the open reading frames encoding the nir, nap and nor genes.

The invention can be more fully understood from the following detailed description and the accompanying sequence descriptions which form a part of this application.

Applicant(s) have provided 14 sequences in conformity with 37 C.F.R. 1.821–1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Adminstrative Instructions). The symbols and format used for nucleotide and amino acid sequence data comply with the rules set forth in 37 C.F.R. §1.822.

SEQ ID NO:1 is the nucleotide sequence of the norb gene encoding the large subunit of the nitric oxide reductase gene isolated from Pseudomonas sp. strain G-179.

SEQ ID NO:2 is the deduced amino acid sequence of the NorB large subunit of the nitric oxide reductase enzyme isolated from Pseudomonas sp. strain G-179.

SEQ ID NO:3 is the nucleotide sequence of the norC gene encoding the small subunit of the nitric oxide reductase gene isolated from Pseudomonas sp. strain G-179.

SEQ ID NO:4 is the deduced amino acid sequence of the NorC small subunit of the nitric oxide reductase enzyme isolated from Pseudomonas sp. strain G-179.

SEQ ID NO:5 is the nucleotide sequence of the norQ gene encoding a nitric oxide reductase assembly protein isolated from Pseudomonas sp. strain G-179.

SEQ ID NO:6 is the deduced amino acid sequence of the NorQ nitric oxide reductase assembly protein isolated from Pseudomonas sp. strain G-179.

SEQ ID NO:7 is the nucleotide sequence of the norD gene encoding a nitric oxide reductase assembly protein isolated from Pseudomonas sp. strain G-179.

SEQ ID NO:8 is the deduced amino acid sequence of the NorD nitric oxide reductase assembly protein isolated from psudomonas sp. strain G-179.

SEQ ID NO:9 is the nucleotide sequence of the mature napA gene encoding the large subunit of the periplasmic nitrate reductase gene isolated from Pseudomonas sp. strain G-179.

SEQ ID NO:10 is the deduced amino acid sequence of the NapA large subunit of the periplasmic nitrate reductase enzyme isolated from Pseudomonas sp. strain G-179. SEQ ID NO:10 includes 18 amino acids comprising a leader sequence not present in the mature protein.

SEQ ID NO:11 is the nucleotide sequence of the napB gene encoding the small subunit of the periplasmic nitrate reductase gene isolated from Pseudomonas sp. strain G-179.

SEQ ID NO:12 is the deduced amino acid sequence of the NapB small subunit of the periplasmic nitrate reductase enzyme isolated from Pseudomonas sp. strain G-179.

SEQ ID NO:13 is the nucleotide sequence of the napC gene encoding an electron transport protein that complements the function of the periplasmic nitrate reductase gene isolated from Pseudomonas sp. strain G-179.

SEQ ID NO:14 is the deduced amino acid sequence of the NapC electron transport protein that complements the function of the periplasmic nitrate reductase enzyme isolated from Pseudomonas sp. strain G-179.

DETAILED DESCRIPTION OF THE INVENTION

The present invention provides new sequences encoding bacterial nitric oxide reductase and bacterial periplasmic nitrate reductase enzymes. The genes and their expression products are useful for the creation of recombinant organisms that have the ability to denitrify toxic waste substances, for the identification of new denitrifying species of bacteria and for fermentation processes in the absence or presence of oxygen. Nucleic acid fragments encoding at least a portion of several of the above mentioned reductase enzymes have been isolated and identified by comparison to public databases containing nucleotide and protein sequences using the BLAST algorithms well known to those skilled in the art.

The supergene cluster containing genes involved in the reduction of nitrate, nitrite, nitric oxide and anaerobic heme biosynthesis was isolated from a denitrifying bacterium Pseudomonas sp. strain G-179 containing a Cu-type nitrate reductase. The nir gene region required for nitrite reduction contained the nitrite reductase structural gene nirU, an unknown nirV, and a regulatory component nnrR. Upstream from the nir region was the napDEFABC gene cluster for the function of periplasmic nitrate reductase. The hemN gene encoding oxygen-independent copropophyringogen III oxidase was located further downstream from the nap region. The next gene cluster was norEFBCQD involved in nitric oxide reduction. The nor region was also linked to another gene cluster that may be involved in uptake or transport function. Mutations in the nor region not only render the strain incapable of using nitrate, nitrite and nitric oxide as the alternative electron acceptor, but also alter its ability to grow on nitrous oxide. This evidence suggests that reduction of nitric oxide and nitrous oxide is functionally linked, and indicates that manipulation of the nor and nir gene cluster will be effective in controlling denitrification. Furthermore a mutation in the nap region abolished the capability for nitrate reduction suggesting that the periplasmic nitrate reductase plays an essential role in denitrification.

In this disclosure, a number of terms and abbreviations are used. The following definitions are provided.

"Open reading frame" is abbreviated ORF.

"Polymerase chain reaction" is abbreviated PCR.

"Cytochrome c oxidase polypetide III" is abbreviated Cox3.

As used herein, "denitrification" refers to the reduction of nitrate ($NO_3^-$) to gaseous intermediates, principally nitrogen gas.

The term "denitrifying bacteria" refers to any bacteria capable of "denitrification".

"Nitric oxide reductase" refers to an integral membrane enzyme of the anaerobic respiratory chain of Pseudomonas sp. strain G-179 that is involved in the denitrification process and specifically catalyzes the reduction of nitric oxide (NO) to nitrous oxide ($N_2O$).

"NorB" and "norB" will refer to the protein and corresponding gene encoding the large subunit of the nitric oxide reductase enzyme.

"NorQ and "norQ" and "NorD" and "norD" will refer to the protein and genes encoding two open reading frames flanking the large and small subunits of the nitric oxide reductase gene, believed to have and effect on the assembly of the Nor proteins.

The term "periplasmic nitrate reductase" refers to an enzyme involved in the denitrification process that catalyzes the reduction of nitrate ($NO_3^-$) to nitrite ($NO_2^-$).

"NapA, NapB and NapC" and "napA, napB and napC" refers to the protein and corresponding genes encoding the large subunit, the small subunit and the electron transport protein, respectively, of the periplasmic nitrate reductase enzyme.

The term "hydropathy" refers to a measurement that shows regions of hydrophobicity or polarity of a protein.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

There term "gene cluster" or "super gene cluster" will mean genes organized in a single expression unit.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences.

For example, it is well known in the art that alterations in a gene which result in the production of a chemically equivalent amino acid at a given site, but do not effect the functional properties of the encoded protein are common. Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1×SSC, 0.1% SDS, 65° C.), with the sequences exemplified herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 90% identical to the identical to the DNA sequence of the nucleic acid fragments reported herein. Most preferred are nucleic acid fragments that are at least 95% identical to the DNA sequence of the nucleic acid fragments reported herein.

A "substantial portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol*. 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular fungal proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default vales" will mean any set of values or parameters which originally load with the software when first initialized.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data. Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG Pileup program found in the GCG program package, as used in the instant invention, using the Needleman and Wunsch algorithm with their standard default values of gap creation penalty=12 and gap extension penalty=4 (Devereux et al., *Nucleic Acids Res.* 12:387–395 (1984)), BLASTP, BLASTN, and FASTA (Pearson et al., *Proc. Natl. Acad. Sci. U.S.A.* 85:2444–2448 (1988). The BLAST X program is publicly available from NCBI and other sources (*BLAST Manual*, Altschul et al., Natl. Cent. Biotechnol. Inf., Natl. Library Med. (NCBI NLM) NIH, Bethesda, Md. 20894; Altschul et al., *J. Mol. Biol.* 215:403–410 (1990)). Another preferred method to determine percent identity, is by the method of DNASTAR protein alignment protocol using the Jotun-Hein algorithm (Hein et al., *Methods Enzymol.* 183:626–645 (1990)). Default parameters for the Jotun-Hein method for alignments are: for multiple alignments, gap penalty=11, gap length penalty=3; for pairwise alignments ktuple=6. As an illustration, by a polynucleotide having a nucleotide sequence having at least, for example, 95% "identity" to a reference nucleotide sequence of SEQ ID NO:1 it is intended that the nucleotide sequence of the polynucleotide is identical to the reference sequence except that the polynucleotide sequence may include up to five point mutations per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO:2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the bacterial reductase enzymes as set forth in SEQ ID NOs: SEQ ID NO:2, SEQ ID NO:4, SEQ ID NO:6, SEQ ID NO:8, SEQ ID NO:10, SEQ ID NO:12 and SEQ ID NO:14. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength.

Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), (hereinafter Maniatis) particularly Chapter 11 and Table 11.1 therein (entirely incorporated herein by reference). The conditions of temperature and ionic strength determine the "stringency" of the hybridization. For preliminary screening for homologous nucleic acids, low stringency hybridization conditions, corresponding to a Tm of 55°, can be used, e.g., 5×SSC, 0.1% SDS, 0.25% milk, and no formamide; or 30% formamide, 5×SSC, 0.5% SDS. Moderate stringency hybridization conditions correspond to a higher Tm, e.g., 40% formamide, with 5× or 6×SSC.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Maniatis supra, 9.50–9.5 1). For hybridizations with shorter nucleic acids, i.e., oligonucleotides, the position of mismatches becomes more important, and the length of the oligonucleotide determines its specificity (see Maniatis supra, 11.7–11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA.

"Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell.

"Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

Genes encoding NapA, B and C proteins as well as NorB, C, Q and D proteins isolated from a denitrifying bacteria have been identified by comparison to the GenBank database using the BLAST algorithms well known to those skilled in the art. NapA showed the highest correlation at the amino acid level, having about 76% identity to to a similar *Paracoccus denitrificans* protein. NapB and NapC had even less identity with only 62% and 66% identity at the amino acid level to *Rhodobacter sphaeroides* and *Paracoccus denitrificans* proteins respectively. Of the nitric oxide reductase proteins, NorQ demonstrated the highest percent identity to a known protein, having 73% identity at the amino acid level to a *Paracoccus halodenitrificans* protein. NorB, Nor C and NorD showed only 66%, 64% and 43% identity respectively at the amino acid level to proteins isolated from *Paracoccus denitrificans*, and *Rhodobacter sphaeroides*.

The nucleic acid fragments of the instant invention may be used to isolate cDNAs and genes encoding homologous enzymes from the same or other bacterial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other nitric oxide reductase (nor) and periplasmic nitrate reductase enzymes (nap), either as cDNAs or genomic DNAs, could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *PNAS USA* 86:5673 (1989); Loh et al., *Science* 243:217 (1989)).

Availability of the instant nucleotide and deduced amino acid sequences facilitates immunological screening cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. *Adv. Immunol.* 36:1 (1984); Maniatis).

The instant nitric oxide reductase and periplasmic nitrate reductase enzymes produced in heterologous host cells, particularly in the cells of microbial hosts, can be used to prepare antibodies to the enzymes by methods well known to those skilled in the art. The antibodies are useful for detecting the enzymes in situ in cells or in vitro in cell extracts. Preferred heterologous host cells for production of the instant nitric oxide reductase and periplasmic nitrate reductase enzymes are microbial hosts. Microbial expression systems and expression vectors containing regulatory sequences that direct high level expression of foreign proteins are well known to those skilled in the art. Any of these could be used to construct chimeric genes for production of the instant nitric oxide reductase and periplasmic nitrate reductase enzymes. These chimeric genes could then be introduced into appropriate microorganisms via transformation to provide high level expression of the enzymes.

Additionally, chimeric genes will be effective in altering the denitrifying properties of the host bacteria. It is expected, for example, that introduction of chimeric nor or nap gene clusters under the control of the appropriate promoters, into a host cell comprising at least one copy of these genes will demonstrate increased denitrifying activity. It is contemplated that it will be useful to express the instant genes both in host cells having pre-existing denitrifying pathways as well as those hosts lacking such pathways. Introduction of nor and nap genes into denitrifying bacteria (such as *Paracoccus denitrificans, Rhodobacter sphaeroides, Thiosphaera pantotropha* and various Pseudomonas sp.) will result in elevated levels of nitric oxide reductase and nitrate reductase, improving the rate of denitrification. Additionally, the instant genes may also be introduced into non-denitrifying bacteria where there are advantages to convey denitrifying properties to a non-denitrifying organism.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the genes encoding the nitric oxide reductase and periplasmic nitrate reductase enzymes in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, trp, $1P_L$, $1P_R$, T7, tac, and trc (useful for expression in *Escherichia coli*).

Termination control regions may also be derived from various genes native to the preferred hosts. Optionally, a termination site may be unnecessary, however, it is most preferred if included.

All or a portion of the nucleic acid fragments of the instant invention may also be used as probes for genetically and physically mapping the genes that they are a part of, and as markers for traits linked to expression of the instant enzymes. For example, the instant nucleic acid fragments may be used as restriction fragment length polymorphism (RFLP) markers. Southern blots (Maniatis) of restriction-digested bacterial genomic DNA may be probed with the nucleic acid fragments of the instant invention. The resulting banding patterns may then be subjected to genetic analyses using computer programs such as MapMaker (Lander et at., *Genonzics* 1:174–181 (1987)) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al., *Am. J. Hum. Genet.* 32:314–331 (1980)).

A variety of nucleic acid amplification-based methods of genetic and physical mapping may be carried out using the instant nucleic acid sequences. Examples include allele-specific amplification, polymorphism of PCR-amplified fragments (CAPS), allele-specific ligation, nucleotide extension reactions, Radiation Hybrid Mapping and Happy Mapping. For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, this is generally not necessary for mapping methods. Such information may be useful in plant breeding in order to develop lines with desired starch phenotypes.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Techniques suitable for use in the following examples may be found in Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D.

Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences were accomplished using either the suite of programs available from the Genetics Computer Group Inc. (Wisconsin Package Version 9.0, Genetics Computer Group (GCG), Madison, Wis.), or BLAST available from NCBI and other sources (*BLAST Manual*, Altschul et al., Natl. Cent. Biotechnol. Inf., Natl. Library Med. (NCBI NIM) NIH, Bethesda, Md. 20894; Altschul et al., *J. Mol. Biol.* 215:403–410 (1990)). In any case where program parameters were not prompted for, in these or any other programs, default values were used.

The meaning of abbreviations is as follows: "h" means hour(s), "min" means minute(s), "sec" means second(s), "d" means day(s), "mL" means milliliters, "L" means liters.

Bacterial Strains and Plasmids:

Table 1 lists all the strains and plasmids used in the instant invention.

raphy equipped with a Ni63 detector (Hewlett Packard 5971, San Fernando, Calif.,).

DNA Manipulation:

Genomic DNA from wild type and mutant strains were isolated with the genomic DNA isolation kit from Qiagen (Santa Clarita, Calif.). To construct the DNA library, the wild type DNA was partially digested with Sau3A and the fractions with DNA above 20 kb were ligated into the BamHI site of SuperCos 1 vector from Strategen (Menasha, Wis.). To isolate the DNA fragments with Tn5 insertions, genomic DNA from different mutant strains were digested with EcoRI and BamHI and ligated to the plasmid pUC18. Positive clones were picked from LB plates containing 50 μg/mL of kanamycin. Inserts from these clones were labeled with the nonradioactive DNA Labeling Kit from Boehringer Mannheim Biochemicals (Indianapolis, Ind.) and used as probes to hybridized the wild type DNA library. Colony hybridization was carried out with the Chemiluminescent Detection Kit (Boehringer Mannheim).

Example 1

Isolation and Gene Organization of the DNA Region Containing Nir, Nap and Nor Gene Clusters Previously, using Tn5 mutagenisis, three types of mutants that were deficient in denitrification were isolated (Ye et al.,

TABLE 1

STRAINS AND PLASMIDS USED IN THIS WORK

| Strain or plasmid | Relevant genotype[a] |
|---|---|
| Strains | |
| RTC01 | Den[+], rifampicin resistant derivative of G-179 |
| RTC07 | norB::Tn5, Tn5 derivative of RTC01, Rif[r], Kan[r] |
| RTC13 | norD::Tn5, Tn5 derivative of RTC01, Rif[r], Kan[r] |
| TW01 | napABC::[Kam], Rif, Kamr |
| Plasmids | |
| pNOREFCB | 3.7 kb Sph I Hind III fragment from pS10 in pSP329 containing norEFCB |
| pNORQD | 4.8 kb Pst I Sph I fragment from pS10 in pSP329 containing norQD |
| pNORD | 2.4 kb EcoR I fragment from pS10 in pSP329 containing norD |

[a]Den = denitrification

Growth Conditions:

Pseudomonas sp. strain G-179 was normally grown in tryptic soy broth (TSB) at 27° C. The concentration for kanamycin was 50 μg/mL if used. The concentrations for tetracycline were 3 and 12 μg/mL, respectively, for broth and solid media. To grow Pseudomonas sp. G-179 strains under denitrifying conditions, potassium nitrate at concentration of 1.5 g/L was used. Conjugation was used to introduced plasmid DNA into the G-179 strains. Conjugation was carried out on TSB plates at 27° C. Exconjugants were selected on TSB plates with rifampicin (50 Pseudomonas sp. strain G-179), kanamycin and tetracyline. For growth on nitrous oxide, TSB in a serum bottle was saturated with nitrous oxide before inoculation and then the gas phase was again filled with the gas.

To induce the denitrification pathway, wild type and mutant strains were first grown on TSB aerobically for 24 h. The cells were then harvested and incubated with TSB supplemented potassium nitrate for additional 24 h. The cells were washed until no nitrate or nitrite was left in the medium before the whole cell assay or crude extract preparation.

Measurement of Nitrate, Nitrite, NO, and $N_2O$:

Both nitrate and nitrite were measured by ion chromatography. NO and $N_2O$ were determined by gas chromatog-

*J. Bacteriol.* 174:6653–6658 (1992)). Type II mutants were deficient in the reduction of nitrite in Pseudomonas sp. strain G-179, leading to the isolation of the Cu-type nitrite reductase structural gene nirU from this organism (Ye et al., *Appl. Environ. Microbiol.* 59:250–254 (1993)). Type I mutants lacked the ability to grow on nitrate, nitrite, and nitrous oxide. It was suggested that mutations in these strains were in the regions responsible for gene regulation or electron transport. To identify the nature of mutations in type I mutants, genomic DNA fragments containing Tn5 insertions from the type I mutant strains RY-7, RY-13, (Ye et al., *Appl. Environ. Microbio.*, supra) were digested with BamHI and EcoRI and cloned into plasmid pUC18. Next, clones resistant to kanamycin were selected. These clones were then used to probe the wild type DNA cosmid library. Three positive cosmid clones were identified containing the nitrite reductase gene.

Sequence analysis from these cosmid clones revealed a 26 kb DNA region containing five gene clusters (FIG. 1). The first gene cluster was the nir region involved in nitrite reduction. The nir region was linked to the nap gene cluster involved in the activity of periplasmic nitrate reductase. Unlike organisms with a heme-type nitrite reductase, the nor gene cluster was not linked directly with the nir region.

Instead, it was located downstream of the nap region. Sequencing results showed that all the type I mutants had Tn5 inserted in the nor gene cluster (Table 1).

Example 2

Analysis of the Derived Gene Products of the Nap Gene Cluster

In the nap gene cluster, the first small ORF was of napE and it was previously identified by comparing the nap cluster from *Paracocuss denitrificans* with the partial sequence upstream of the nirU gene of Pseudomonas sp. strain G-179 (Berk et al., *J. Bacteriol.* 179:6769–6777 (1995)). The function of napE remains unknown.

The gene product of second ORF had 166 residues with a molecular weight of 18 Kda. It showed about 30% identity with the ferrodoxin-type electron transport protein NapF from *Escherichia coli* (JŸngst et al., *FEBS Lett.* 314:308–314 (1992)). The cysteine residues involved in the binding of 4Fe-4S centers were conserved. Following napF was napD with an ORF that encoded a protein with 25% identity to the putative cytoplasmic protein NapD from *Paracoccus denitrificans* (Berk et al., *J. Bacteriol.* 179:6769–6777 (1995)). Both napD and napF were also present in the front of napA in *Escherichia coli* (JŸngst et al., *FEBS Lett.* 314:308–314 (1992)). The NapD protein has not been characterized and its function remains unknown.

The derived protein product from the ORF after napD was napA, which had about 70% identity to the large subunit of periplasmic nitrate reductase from *Paracoccus denitrificans* (Berk et al., *J. Bacteriol.* 179:6769–6777 (1995)). The mature protein should have 804 amino acids with a predicted molecular weight of 90 Kda. Hydropathy analysis indicated that the mature NapA was hydrophilic. These analyses suggested NapA of Pseudomonas sp. strain G-179 was located in the periplasmic space, similar to other NapA proteins. The nucleotide sequence of the ORF for napA and its predicted primary amino acid sequence are set forth in SEQ ID NO:9 and SEQ ID NO:10, respectively.

Subsequently, it was determined that the derived gene products of both the napB and napC genes of Pseudomonas sp. strain G-179 were similar to NapB, the small subunit of nitrate reductase, and NapC, a putative electron transport protein. NapB and NapC contain binding sites for cytochrome C. The napB gene of Pseudomonas sp. strain G-179 appeared to have a leader peptide and alanine-32 of the NapB precursor could be the first residue of the mature protein. The nucleotide sequence of the ORF for napB and its predicted primary amino acid sequence are set forth in SEQ ID NO:11 and SEQ ID NO:12, respectively. NapC had a N-terminal spanning region and binding site for cytochrome c, suggesting it was a membrane-anchored cytochrome. The nucleotide sequence of the ORF for napC and its predicted primary amino acid sequence are set forth in SEQ ID NO:13 and SEQ ID NO:14, respectively.

Example 3

Analysis of the Derived Gene Products of the Nor Gene Cluster and Unknown Adjacent Gene Cluster The nor gene cluster contained norC, which encodes the small subunit of the nitric oxide reductase. The nucleotide sequence of the ORF for norC and its predicted primary amino acid sequence are set forth in SEQ ID NO:1 and SEQ ID NO:2, respectively. The norB gene encoding the large subunit of the nitric oxide reductase was located immediately after the norC gene. The nucleotide sequence of the ORF for norC and its predicted primary amino acid sequence are set forth in SEQ ID NO:3 and SEQ ID NO:4, respectively.

The gene product of norQ had 265 residues and had a calculated molecular biomass of 29 Kda. The nucleotide sequence of the ORF for norQ and its predicted primary amino acid sequence are set forth in SEQ ID NO:5 and SEQ ID NO:6, respectively. The amino acid sequence of NorQ from Pseudomonas sp. strain G-179 was similar to those found in *Paracoccus denitrificans* (Bartnikas et al., *J. Bacteriol.* 179:3534–3540 (1997)), *Rhodobacter sphaeroides* (Grove et al., *Mol. Microbiol.* 19:467–481 (1996)) and *Pseudomonas stutzeri* (Zumft et al., *Eur. J. Biochem.* 219:481–490 (1994)), respectively.

Following the norQ was the norD ORF that had 632 residues with a molecular mass of 72 Kda. The nucleotide sequence of the ORF for norD and its predicted primary amino acid sequence are set forth in SEQ ID NO:7 and SEQ ID NO:8, respectively. This protein can be separate into two regions. The N-terminal half of the protein showed some homology to a portion of the Maize UDP-glucose flavonoid 3-O-glucosyltransferase (Ralston et al., (1988), *Genetics*, 119, 185), while the C-terminal half had some similarity to the potassium uptake protein TrkA from *Escherichia coli* (Reizer et al., *Res. Microbiol.* 141:1069–1072 (1990)). TrkA binds to AND(H) and arginine-234 and arginine-262 of TrkA have been suggested to be the potential binding ligands. These two arginine residues were also conserved in NorD proteins from Pseudomonas sp. strain G-179, and other denitrifying bacteria (Bartnikas et al., *J. Bacteriol.* 179:3534–3540 (1997); Grove et al., *Mol. Microbiol.* 19:467–481 (1996)). NorD also showed some similarity to the yojO gene product from *Bacillus subtilis*.

Table 2 lists the present Nap and Nor proteins and their correlation with the most similar known proteins found in public databases.

TABLE 2

COMPARISON OF AMINO ACID SQUENCES

| Proteins (G179) | % amino acid identity* | Accession # | Database | Protein | Reference |
|---|---|---|---|---|---|
| NapA | 76 | Q56350 | Swissprot | NapA_ParDt | Berks, B. C., Biochem. J. 309: 983–992 (1995) |
| NapB | 62 | Q53177 | Swissprot | NapB_RhoSh | Reyes, F., Mol. Microbiol. 19: 1307–1318 (1996) |
| NapC | 66 | Q56352 | Swissprot | NapC_ParDt | Berks, B. C., Biochem, J. 309: 983–992 (1995) |
| NorC | 66 | U28078 | Genbank | NorC_ParDt | de Boer, A. P. N., Unpublished |

TABLE 2-continued

COMPARISON OF AMINO ACID SQUENCES

| Proteins (G179) | % amino acid identity* | Accession # | Database | Protein | Reference |
|---|---|---|---|---|---|
| NorB | 64 | AF000233 | Genbank | NorB_RhoSh | Bartnikas, T. J., Bacteriol. 179 (11), 3534–3540 (1997) |
| NorQ | 73 | AB010889 | Genbank | NorQ_ParHDt | Sakurai, N., Biochem. Biophys. Res. Commun. 243 (2), 400–406 (1998) |
| NorD | 43 | U28078 | Genbank | NorD_ParDt | de Boer, A. P. N., Unpublished |

*% Identity calculated using default values with the BLAST X available from NCBI and other sources (BLAST Manual, Altschul et al., Natl. Cent. Biotechnol. Inf., Natl. Library Med. (NCBI NLM) NIH, Bethesda, Md. 20894; Altschul et al., J. Mol. Biol. 215: 403–410 (1990))

Example 4

Functional Characterization of the Nap and Nor Gene Cluster

To determine whether the nap region had a role in the conversion of nitrate to nitrate under denitrifying conditions, a sal I and Bgl II fragment in the nap region was deleted and replaced with the Kam-resistant cassette. The resulting mutant strain TW01 showed no growth with nitrate as the alternative electron acceptor under denitrifying conditions. The 5.5 kb Kpn I-Hind III fragment contain the napEFABC region was able to restore the ability of strain TW01 to grow on nitrate as the electron acceptor. This result demonstrated that the nap region was required for reduction of nitrate.

Mutations in the nor region in other denitrifying bacteria have been shown to have a detrimental effect on their ability to denitrify $NO_3^-$ and $NO_2^-$ due to the accumulation of toxic NO. All the type II mutants of Pseudomonas sp. strain G-179, which had Tn5 inserted in the norB (RTC07) or the norD gene (RTC13, RTC14, RTC23, and RTC29), exhibit similar characteristics (Ye et al., *J. Bacteriol.* 174:6653–6658 (1992)). To define the regions that are necessary to restore the function of Nor-mutants RTC07 and RTC13, the 8.2-kb SphI fragment containing the norEFCBQD gene cluster was used for complementation studies. This fragment complemented both RTC07 and RTC13. Under the control of the lacZ promoter, the 4.8 kb PstI-SphI fragment containing both norQ and norD or the 2.4 kb EcoRI fragment containing norD alone restored the denitrifying capability of RTC13. This result clearly suggests that the norEFCBQD genes are necessary for denitrification.

The effect of mutations in the nor region on the ability to reduce $N_2O$ was further examined in this study. Both wild type and mutant strains were inoculated into a TSB medium saturated with $N_2O$. For the wild type, significant growth was observed after two days of incubation. For strain RTC13, growth was not apparent until four days later. The lag period was longer for strain RTC13. No lag phase was observed when RTC 13 and RTC07 were complemented by pNorD and pNorEFCBQD, respectively. Strain RT07 could not be complemented by either DNA fragments with norEFBC or norQD. These results suggest that mutations in the nor region cause a delay in the ability to grow on $N_2O$ as the alternative electron acceptor.

What is claimed is:

1. An isolated nucleic acid fragment encoding an enzymatically active bacterial periplasmic nitrate reductase subunit, wherein said enzymatically active bacterial periplasmic nitrate reductase comprises NapA, NapB, NapC subunits selected from the group consisting of:
   (a) an isolated nucleic acid fragment encoding the amino acid sequence selected from the group consisting of SEQ ID NO:10, SEQ ID NO:12 and SEQ ID NO:14;
   (b) an isolated nucleic acid fragment having at least 90% identity with the nucleic acid sequence selected from the group consisting of SEQ ID NO:9, SEQ ID NO:11, and SEQ ID NO:13; and
   (c) an isolated nucleic acid fragment that hybridizes with SEQ ID NO:9, SEQ ID NO:11, and SEQ ID NO:13 under the following hybridization conditions: 0.1×SSC, 0.1% SDS, 65° C.; or
   an isolated nucleic acid fragment that is complementary to (a), (b), or (c).

2. The isolated nucleic acid fragment of claim 1 selected from the group consisting of SEQ ID NO:9, SEQ ID NO:11 and SEQ ID NO:13.

3. A chimeric gene comprising the isolated nucleic acid fragment of claim 1 operably linked to suitable regulatory sequences.

4. A transformed host cell comprising the chimeric gene of claim 3.

5. The transformed host cell of claim 4 wherein the host cell is selected from the group consisting of bacteria, yeast and filamentous fungi.

6. The transformed host cell of claim 4 wherein the host cell is selected from the group consisting of Escherichia, Bacillus, Yeast and denitrifying bacteria.

7. A nucleic acid fragment encoding the amino acid sequence of an enzymatically active bacterial periplasmic nitrate reductase subunit obtained by the method comprising:
   (a) probing a genomic library with the nucleic acid fragment of claim 1;
   (b) identifying a DNA clone that hybridizes under stringent conditions of 0.1×SSC, 0.1% SDS, 65° C. with the nucleic acid fragment of claim 1; and
   (c) sequencing the genomic fragment that comprises the clone identified in step (b), wherein the sequenced genomic fragment encodes an enzymatically active bacterial periplasmic nitrate reductase subunit, wherein said enzymatically active bacterial periplasmic nitrate reductase comprises NapA, NapB, and NapC subunits.

* * * * *